United States Patent [19]

Theeuwes

[11] Patent Number: 4,871,360
[45] Date of Patent: * Oct. 3, 1989

[54] SYSTEM FOR INTRAVENOUS DELIVERY OF A BENEFICIAL DRUG AT A REGULATED RATES

[75] Inventor: Felix Theeuwes, Los Altos, Calif.

[73] Assignee: Alza Corporation, Palo Alto, Calif.

[*] Notice: The portion of the term of this patent subsequent to Mar. 27, 2001 has been disclaimed.

[21] Appl. No.: 854,452

[22] Filed: Apr. 21, 1986

Related U.S. Application Data

[63] Continuation of Ser. No. 588,165, Mar. 9, 1984, which is a continuation of Ser. No. 312,491, Oct. 19, 1981, Pat. No. 4,552,555, which is a continuation-in-part of Ser. No. 289,082, Jul. 31, 1981, abandoned.

[51] Int. Cl.$^4$ ............................................. A61K 9/22
[52] U.S. Cl. ................................. 604/892.1; 604/56; 604/85
[58] Field of Search ................................ 604/80–86, 604/416, 890, 892, 246, 257, 258, 27, 30, 48, 56

[56] References Cited

U.S. PATENT DOCUMENTS

| | | | |
|---|---|---|---|
| Re. 25,129 | 2/1962 | Walter | 604/252 |
| 911,523 | 2/1909 | Piers | 604/92 X |
| 1,654,745 | 1/1928 | Miller | 604/80 |
| 2,682,268 | 6/1954 | Ryan et al. | 604/252 X |
| 2,690,179 | 9/1954 | Fox | 604/87 |
| 2,849,256 | 8/1958 | Kowal | 604/80 |
| 2,954,028 | 9/1960 | Smith . | |
| 3,001,525 | 9/1961 | Hendrick . | |
| 3,305,446 | 2/1967 | Bechtol et al. | 167/72 |
| 3,322,114 | 5/1967 | Portnoy et al. . | |
| 3,756,237 | 9/1973 | Chittenden et al. . | |
| 3,756,390 | 2/1973 | Abbey et al. | 206/47 A |
| 3,760,984 | 9/1973 | Theeuwes | 222/95 |
| 3,797,485 | 3/1974 | Urquhart . | |
| 3,797,494 | 3/1974 | Zaffaroni . | |
| 3,845,770 | 11/1974 | Theeuwes et al. . | |
| 3,847,150 | 11/1974 | Scheuermann | 128/229 |
| 3,848,603 | 11/1974 | Throner . | |
| 3,854,480 | 12/1974 | Zaffaroni . | |
| 3,921,635 | 11/1975 | Gauthier . | |
| 3,921,636 | 11/1975 | Zaffaroni . | |
| 3,941,126 | 3/1976 | Dietrick et al. . | |
| 3,948,254 | 4/1976 | Zaffaroni . | |
| 3,976,068 | 8/1976 | Lindquist . | |
| 3,993,066 | 11/1978 | Virag . | |
| 3,993,072 | 11/1975 | Zaffaroni . | |
| 3,993,073 | 11/1975 | Zaffaroni . | |
| 3,995,631 | 12/1976 | Higuchi . | |
| 4,061,141 | 12/1977 | Hydes . | |

(List continued on next page.)

FOREIGN PATENT DOCUMENTS 497181 9/1969 Switzerland .
982107 9/1963 United Kingdom .

OTHER PUBLICATIONS

Paxinos, J. and Samuels, T. M.: *Am J Hosp Pharm*, vol. 32, pp. 892–897.

Goodwing, H. N., *The American Journal of I. V. Therapy*, pp. 27–30, Dec.–Jan. 1975.

Masson, A. H. B., *Brit J. Anaesth.*, vol. 43, pp. 681–686, (1971).

Ferenchak et al., *Surgery*, vol. 70, No. 5, pp. 674–677, Nov. 1971.

Primary Examiner—C. Fred Rosenbaum
Assistant Examiner—Mark O. Polutta
Attorney, Agent, or Firm—Paul L. Sabatine; Edward L. Mandell; Steven F. Stone

[57] ABSTRACT

A formulation chamber is disclosed comprising a wall surrounding a space containing a beneficial agent. The formulation chamber has an inlet for admitting a fluid into the chamber and an outlet for letting the fluid containing the agent leave the chamber. The chamber can additionally comprise a film for regulating the rate of release from the chamber, and optionally a filter. The chamber is adapted for use in an intraveous delivery system for delivering the fluid containing the agent to a patient. A method also is disclosed for using the formulation chamber.

6 Claims, 3 Drawing Sheets

U.S. PATENT DOCUMENTS

| | | | |
|---|---|---|---|
| 4,105,092 | 8/1978 | Virag | 128/260 |
| 4,116,646 | 9/1978 | Edwards | 55/159 |
| 4,177,256 | 12/1979 | Michaels et al. | 424/22 |
| 4,200,095 | 4/1980 | Reti | 128/214 |
| 4,203,439 | 5/1980 | Theeuwes . | |
| 4,217,894 | 8/1980 | Franetzki . | |
| 4,233,973 | 11/1980 | Shukla . | |
| 4,235,236 | 11/1980 | Theauwes | 128/260 |
| 4,236,517 | 12/1980 | Langston et al. . | |
| 4,256,104 | 3/1981 | Muetterties et al. . | |
| 4,321,117 | 3/1982 | Kaetsu et al. | 204/159 |
| 4,323,457 | 4/1982 | Sun et al. | 210/645 |
| 4,424,056 | 1/1984 | Urguhart et al. | 604/56 |
| 4,465,471 | 8/1984 | Harris et al. | 604/56 |
| 4,479,794 | 10/1984 | Urguhart et al. | 604/85 |
| 4,525,162 | 6/1985 | Urgahart et al. | 604/56 |
| 4,533,348 | 8/1985 | Wolfe et al. | 604/85 |
| 4,552,555 | 11/1985 | Theeuwes | 604/85 |

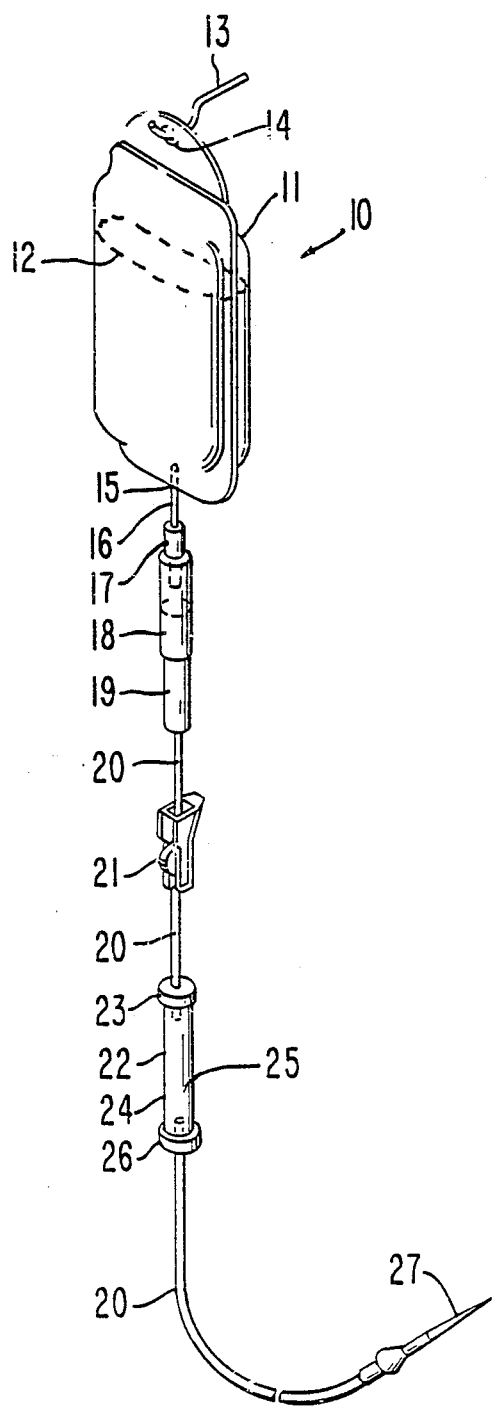
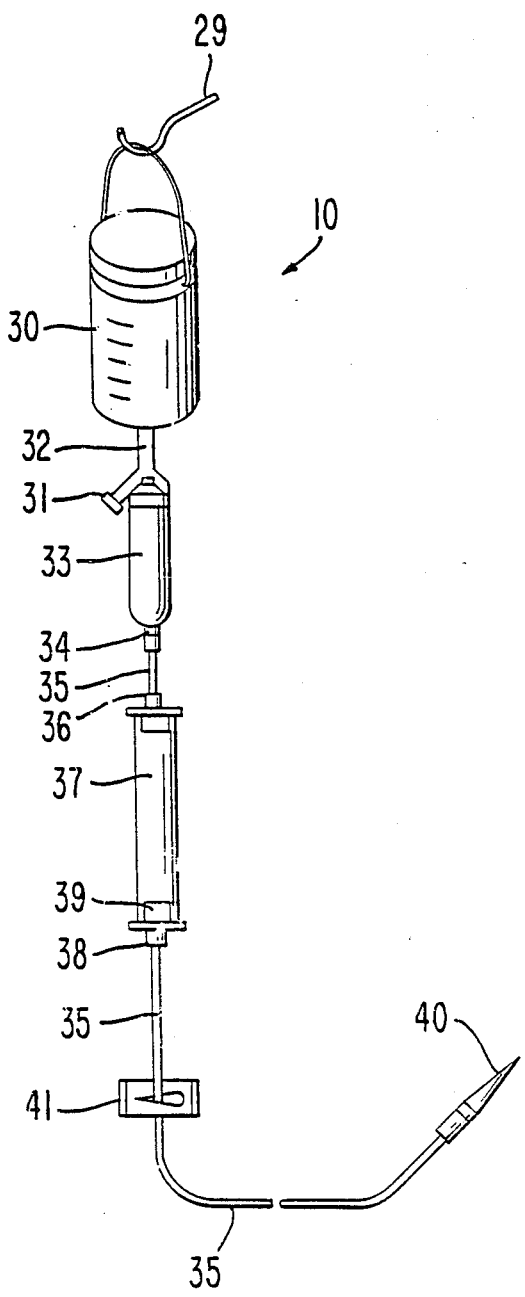

SYSTEM FOR INTRAVENOUS DELIVERY OF A BENEFICIAL DRUG AT A REGULATED RATES

CROSS REFERENCE TO RELATED APPLICATION

This is a continuation of application 06/588,165 filed Mar. 9, 1984, which application is a continuation of application 06/312,491 filed Oct. 19, 1981 now U.S. Pat. No. 4,552,555 issued Nov. 12, 1985, which application 06/312,491 is a continuation-in-part of 06/289,082 filed July 31, 1981 abandoned, which application 06/588,165 is copending with application 06/310,047 filed Oct. 9, 1981 now U.S. Pat. No. 4,511,353 issued Apr. 16, 1985, which applications are incorporated herein by reference and benefit is claimed of their filing dates. All of these applications are assigned to ALZA Corporation of Palo Alto, Calif.

FIELD OF THE INVENTION

This invention pertains to both an intravenous delivery system and to a formulation chamber containing a beneficial agent. The invention also relates to a method of administering intravenously a beneficial agent using the intravenous delivery system comprising the agent formulation chamber, and to a method for adding an agent to a fluid.

BACKGROUND OF THE INVENTION

The parenteral administration of medical liquids is an established clinical practice. The liquids are administered particularly intravenously, and the practice is used extensively as an integral part of the daily treatment of medical and surgical patients. The liquids commonly administered include blood and blood substitutes, dextrose solution, electrolyte solution, and saline. Generally the liquids are administered from an intravenous delivery system having a container suspended above the patient, with the liquid flowing through a catheter hypodermic needle set to the patient.

The administration of liquids intravenously is a valuable and important component that contributes to the optimal care of the patient, however, it does not provide a satisfactory means and method for administering concomitantly therewith a beneficial agent. Presently, a beneficial agent is administered intravenously by (1) temporarily removing the intravenous system and halting the flow of liquid, and then intravenously administering the agent to the patient followed by reinserting the intravenous system into the patient; (2) the agent is added to the liquid in the container and then carried by the flow of the liquid to the patient; (3) agent is added to a liquid in a separate container called a partial fill that is connected to the primary intravenous line through which line the agent is carried by the flow of liquid to the patient; (4) an agent is contained in a piggyback vial into which is introduced an intravenous fluid, with the vial subsequently connected to the primary line through which the drug is administered to the patient; or (5) the agent is administered by a pump that exerts a force on a liquid containing agent for intravenously administering the liquid containing the agent. While these techniques are used, they have major disadvantages. For example, the administration of an agent through repeated insertion of a needle leads to unnecessary pain and trauma, they require separate connections for joining the primary intravenous line which further complicates intravenous administration, the use of pumps can produce pressures that can vary at the delivery site and the pressure can give rise to thrombosis, the rate of agent delivery to the patient often is unknown as it is not rate-controlled agent delivery but dependent on the flow of fluid, and they often require preformulation of the agent medication by the hospital pharmacist or nurse. In view of this presentation, it is immediately apparent a critical need exists in the field of intravenous delivery for a hospital acceptable and dependable manufacture and method for administering a beneficial agent at a controlled rate in intravenous delivery systems.

DISCLOSURE OF THE INVENTION

Accordingly, a principal object of this invention is to provide an intravenous delivery system for administering a beneficial agent at a controlled rate and in an improved manner for optimizing the care of a human whose prognosis benefits from intravenous delivery of a beneficial agent.

Another objectof the invention is to provide an intravenous delivery system comprising a formulation chamber containing a beneficial agent for admitting the agent into an intravenous fluid for optimizing the care of a patient on intranveous therapy.

Another object of the invention is to provide a formulation chamber containing a beneficial agent and which chamber is adapted for use in an intravenous delivery system for admitting a beneficial agent at a controlled rate of dissolution into an intravenous fluid admitted into the chamber.

Another object of the invention is to provide an intravenous delivery system comprising an agent formulation chamber housing a benefical agent and a rate controlling membrane for delivery an agent formulation at a rate governed by the rate controlling membrane into recipient.

The invention concerns an intravenous delivery system and an agent formulation chamber which formulation chamber is adapted for use wlth the system. The formulation chamber contains a beneficial agent that is formulated with an intravenous fluid entering the chamber in situ, and then infused into a recipient. The invention also is an intravenous delivery system for administering a fluid agent formulation, wherein the fluid agent formulation is formulated in situ and wherein the intravenous delivery system comprises in combination: (a) a container for storing a pharmaceutically acceptable fluid which is also a pharmaceutically acceptable carrier for the agent; (b) a formulation chamber comprising a wall surrounding a lumen, and having a surface inlet that permits communication with the container to let a fluid flow from the container into the formulation chamber, and an outlet surface through which an agent formulation exits the chamber; (c) a beneficial agent in the chamber; and, (d) a conduit that communicates with the chamber outlet and extends to a patient recipient site.

BRIEF DESCRIPTION OF THE DRAWINGS

In the drawings, which are now drawn to scale, but are set forth to illustrate various embodiments of the invention, the Figures are as follows:

FIG. 1 is a perspective view showing an embodiment of the invention comprising an intravenous delivery system comprising a formulation chamber;

FIG. 2 is a perspective view showing another embodiment of the invention comprising an intravenous delivery system and a formulation chamber;

In the specification and the drawings, like parts in related Figures are identified by like numbers. The terms appearing earlier in the specification and in the description of the drawings are described hereafter in the disclosure.

MODES FOR CARRYING OUT THE INVENTION

Figure 3:
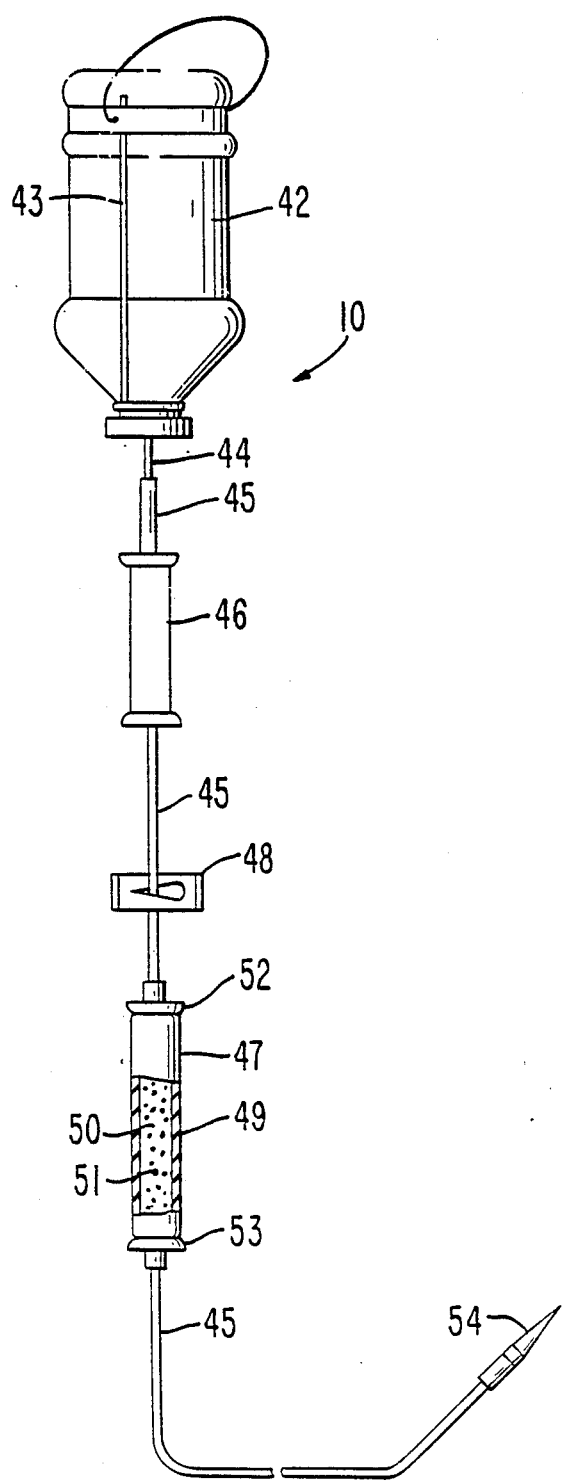
FIG. 3 is a perspective view showing another embodiment of the invention comprising a complete intravenous delivery system for delivering a beneficial agent solution.

FIG. 1 illustrates an operative intravenous delivery system provided by the invention and it is generally designated by the numeral 10. System 10 comprises a container 11 formed of a flexible, or a semi-rigid, preferrably transparent plastic, such as polyvinylchloride, or a polyolefin, and it contains a medical fluid 12 adapted for intravenous administration. Medical fluid 12 in container 11 will typically be a sterile solution, such as an aqueous solution of dextrose, a solution of dextrose in saline, an electrolyte solution and saline. Medical fluid 12 also is a pharmaceutical vehicle or carrier for intravenous administration, and it is a pharmaceutical carrier for a beneficial agent that is to be administered to a recipient. Container 11, in the embodiment illustrated, is non-vented, the medical fluid in it is at atmospheric pressure, and the container collapses as it empties of fluid 12. Container 11 usually is adapted to be hung neck-down from a hanger 13 by a bib or hole 14 that connects or is integrally formed as part of container 11. Container 11, at its end distance from its hanging end, that is, at its neck end has an administration port 15 adapted for receiving an administrative set.

The administration set provided by this invention is used to deliver fluid 12 and a beneficial agent admitted into intravenous delivery system 10 to a patient. The administration set is sterile, pyrogen-free and disposable. The administration set comprises the components described hereafter, and it connects with port 15 of container 11. Port 15 can be a diaphragm in container 11, not shown, or port 15 can be a hollow connector 16. Connector 16 is adapted to receive end 17 of drip chamber 18, which end 17 fits snugly over connector 16. Drip chamber 18 is used to trap air and permit adjustment of the rate of flow of fluid 12 from container 11 as the flow proceeds drop wise. An outlet 19 of drip chamber 18 is connected to a first segment of tubing 20 that fits into outlet 19. An adjustable clamp 21 of the roller or screw type on tubing 20 pinches the internal diameter of tubing 20 to regulate flow in cooperation with drip sight chamber 18. A second segment of tubing 20 connects to inlet 23 of agent formulation chamber 22. A third segment of tubing 20 connects to outlet 26 of formulation chamber 22 and to an adapter-needle assembly 27 that is inserted into a vein and sometimes an artery of a warm-blooded animal.

Agent formulation chamber 22 is a unique component of the intravenous delivery system both as the chamber alone and in combination with the system. Formulation chamber 22 is sized and adapted for use in intravenous systems, it is self-contained, self-priming, self-powered and amenable to low cost manufacturing. Formulation chamber 22 contains an intravenously administratable beneficial agent, and the use of formulation chamber 22 with agent therein does not require any reconstitution or admixture prior to use. Agent formulation chamber 22 is a lightweight disposable chamber comprising a wall 24 that surrounds and defines an internal space or lumen 25. Chamber 22 has an inlet 23 adapted and sized for placing chamber 22 into an intravenous delivery system, and it has an outlet 26 also adapted for placing the chamber in the system. Inlet 23 and outlet 26 are made for receiving tube 20. Chamber 22 is made of glass, plastic or the like, and as illustrated it is made of a transparent material for illustrating its structure and an agent housed therein. The agent in chamber 22 can be in any pharmaceutical state that forms an agent formulation with the fluid that enters the chamber. Exemplary pharmaceutically acceptable forms include solid, crystaline, microcrystalline, particle, pellet, granule, powder, tablet, spray-dried, lyophilized, compressed forms that undergo disintegration and dissolution in the presence of an intravenous fluid such as compressed particles, compressed powders, compressed granules, friable layers of agent, and the like. Agent formulation chamber 22 generally will store an amount of agent for executing a prescribed therapeutic or beneficial program. That is, an amount of agent for the preprogrammed, unattended delivery of a therapeutically or a beneficially effective amount of the agent to produce a therapeutic or a beneficial result. Agent formulation chamber 22 generally will have a capacity of from about 10 milliliters to 250 milliliters of fluid or more, and it can house from about 5 milligrams to 20 grams of agent or more. The expression beneficial agent, as used herein, generally denotes any substance that produces a therapeutic or a beneficial result, such as a drug, a carbohydrate, an electrolyte and/or the like. The term fluid or liquid denotes a fluid or liquid that can be administered parenterally including intravenously, comprising pharmaceutically acceptable fluids that are also a pharmaceutically acceptable carrier for an agent, such as water, isotonic saline, Ringer's lactate, and the like. The term formulation, and agent formulation as presently used herein, generically indicates the benefical agent is formulated, mixed, added, dissolved, suspended, carried, and/or the like in or by the fluid in a physical-chemical form acceptable for parenteral including intravenous administration. In an additional embodiment of the invention, formulation chamber 22 can simultaneously act as a drip chamber while housing an agent. In this embodiment, the formulation chamber-drip chamber is used to achieve a desired fluid drop rate. For example, the formulation chamber-drip chamber can have a fast drop rate for adults, or it can have a slower drop rate for pediatric use. The formulation chamber-drip chamber can be made with various sized inlets for controlling the rate of drip, or the drip can be controlled by a regulating clamp on the tubing conveying fluid thereto. The formulation chamber-drip chamber can deliver, for example from 2 to 75 drops per milliliter over from 1 minute to 1 hour. More preferably, the therapist can adjust the rate of flow of 1 to 20 drops per minute, or for the need of the patient. An additional disclosure pertaining to formulation chamber 22 is presented later in this specification.

FIG. 2 illustrates another operative intravenous therapeutic system generally designated 10 as provided by the invention and supported in delivery position by support 29. System 10 is a vented-type system that requires air to operate. System 10 comprises a glass container 30 suitably sealed with a rubber stopper, not showing, and it contains a fluid designed for intravenous administration. Air enters system 10 via an air filter 31 connected to container 30 through spike 32 that is hollow and pierces the rubber closure of container 30. The other point of spike 32, not seen, enters drip chamber 33 and conveys the fluid from container 30 to drip chamber 33. Drip chamber 33 is connected to an agent formulation chamber 37 through a first section of tubing 35 inserted into end 34 of drip chamber 33 and also inserted into formulation chamber end 36 adapted for receiving tube 35. The other end 38 of formulation chamber 37 also is adapted for receiving tube 35. Formulation chamber 37 is made of glass or plastic, and it is preferably transparent. Formulation chamber 37 can have any shape adapted for use in an intravenous delivery system, and it is preferably round and its length exceeds its width. Ends 36 and 38 fit snugly into chamber 37 to form an air-tight, leak-proof closure for containing at least one agent, and an agent solution formed in situ in chamber 37 by fluid entering from container 30 and mixing or dissolving therein. Chamber 37 optionally is equipped with a release rate controlling membrane 39, for example a microporous polymeric membrane or the like, that governs the rate of release of agent solution from chamber 37. Membrane 39 can rest on a sintered glass support, not shown, integrally made into chamber 37, membrane 39 can adhesively be sealed to the inside wall of chamber 37, fused thereto, be supported by wall of the chamber pinched inwardly, on a rim in the chamber, or it can be supported or suitably fixed to end cap 38. Optionally, chamber 37 can be equipped with a release rate controlling membrane at its inlet for governing fluid flow into chamber 37. A second section of tubing 35 conveys a solution containing agent from chamber 37 to needle 40. A pinch clamp 41 is provided for pinching the internal diameter of tubing 35 to regulate the flow.

FIG. 3 illustrates another intravenous system 10 provided by the invention. System 10 comprises in combination a container 42 that is reservoir of a pharmaceutically acceptable fluid and it has an internal venting tube 43 which allows air to enter the container as medical fluid is infused into a patient. Container 42 is closed with a stopper, not shown, and it has a hole for venting tube 43. Container 42 is connected through a non-vented hollow spike adaptor 44 to the intravenous system for sending medical fluid from container 42 through system 10 to a patient. Spike 44 connects to a first section of tubing 45 that enters into a drip chamber 46. Drip chamber 46 is, as previously described, made preferably of a see through material such as glass or a plastic for visibly counting a measurable number of drops that pass through said chamber over unit time. A second section of tubing unites drip chamber 46 with a formulation chamber 47. The second section of tubing 45 passes through a clamp 48 used for regulating flow. Formulation chamber 47 comprises a wall 49 that surrounds an internal space 50. Chamber 47, houses in space 50, a dosage unit amount of agent 51, as represented by dots, for performinf a beneficial program. Agent 51 is present in a pharmaceutically acceptable form that can undergo dissolution, or it can disintegrate into smaller parts and dissolve in the presence of liquid in chamber 47 to form an agent solution. The chamber 47 can optionally contain a filtering element for providing a sterile fluid by removing particulate matter and/or bacteria from the fluid, which element does not interfer with the rate of fluid passing through the chamber. Delivery from such system can be controlled, for example, by the rate of dissolution as governed by particle size of agent and the solubility of the agent in the fluid. Chamber 47 has an end 52 for receiving incoming tube 45 and the medical fluid from container 42, and it has an end 53 for receiving outgoing tube 45. Tube 45 carries the agent solution from chamber 47 comprising a beneficially effective amount of agent 51 through needle 54 to a patient for producing the intended beneficial effect.

Figure 4:
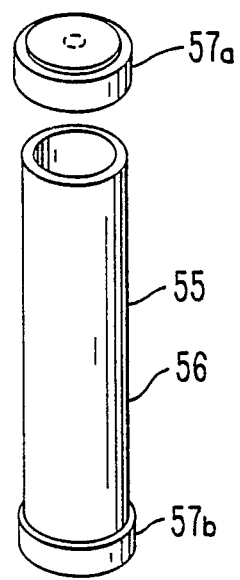
FIG. 4 is a perspective view of a formulation chamber provided by the invention, which chamber is adapted and designed for use in an intravenous delivery system.
Figure 5:
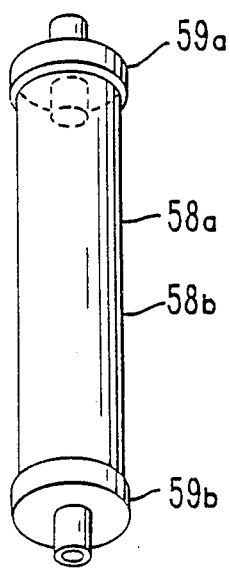
FIG. 5 is a perspective view of a formulation chamber useful for forming a solution containing a beneficial agent in the chamber, and which chamber is shaped and sized for use in an intravenous delivery system.

FIGS. 4 through 8 depict structural embodiments of formulation chambers that can be used in the intravenous delivery system of FIGS. 1 to 3. FIG. 4 illustrates a formulation chamber 55 that is light weight, disposable and indicated for use in patients requiring intravenous administration of a fluid containing a beneficial agent. In FIG. 4, chamber 55 comprises a body 56 of tube shape and it has a pair of caps 57a and 57b for forming a closed chamber for containing fluid and agent. Caps 57a and 57b fit body 56 and they are preferably made of self-sealing rubber through which a needle or hollow spike can be inserted, or of rubber with a pre-drilled hole covered by a latex disc through which communication can be made with the inside chamber 55. Formulation chamber 55 can preferably be hermetically sealed, is moisture proof, microorganism impermeable, ionizing ray permeable and adapted to contain agent in dry form for mixing with an incoming fluid including aqueous and non-aqueous fluids. FIG. 5 depicts a formulation chamber 58a that is similar in structure to chamber 55 of FIG. 4. Chamber 58a comprises a hollow body 58b for containing an agent and medical fluid, and it has a pair of closures 59a and 59b that fit over body 58b. The closures each have a hollow member, that is preferably round for receiving a tube that can slide into, or slide over the member.

Figure 6:
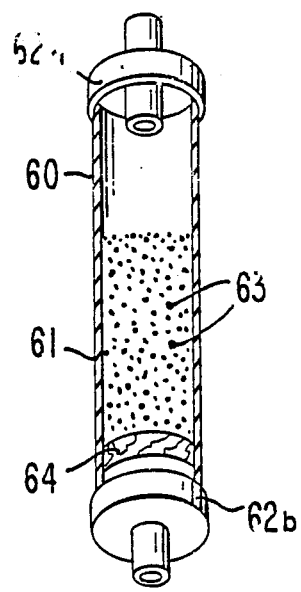
FIG. 6 is an opened view of a beneficial agent formulation chamber comprising a beneficial agent and a flow controlling membrane for governing the rate of fluid passage and the accompanying rate of drug passage through the chamber.
Figure 7:
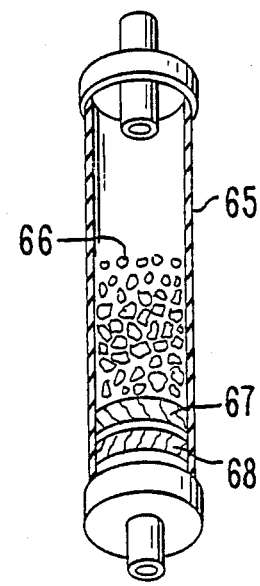
FIG. 7 is an opened view of a formulation chamber comprising a beneficial agent, a flow controlling membrane, and a filter; and, FIG. 8 is an opened view of a formulation chamber manufactured with an agent containing compartment.
Figure 8:
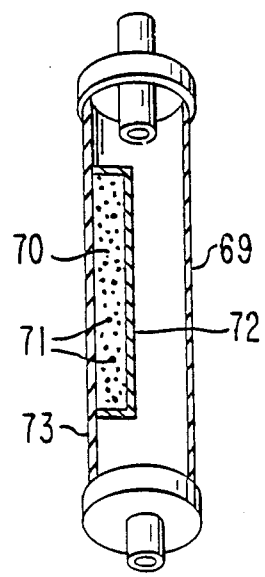

FIGS. 6 through 8 illustrate formulation chambers with a section removed for depicting the inside of the chambers. In FIG. 6, chamber 60 comprises a wall 61 with a section removed and ends 62a and 62b. Chamber 60 contains agent 63 that is soluble in intravenously acceptable fluids and film 64 formed of a material for controlling the flow of fluid and agent from chamber 60. Film 64 in a preferred embodiment is formed of an agent release rate controlling polymer, such as a microporous polymer like a polycarbonate, a semipermeable polymer like cellulose acetate, or a diffusional polymer like ethylene-vinyl acetate copolymer. The polymeric film according to the mode of the invention is used in a presently preferred embodiment for governing the rate of release of solution containing agent from chamber 60, that is, agent release and fluid flow through chamber 60. Chamber 60 is illustrated with a film at its exit, and optionally it can have a film at its inlet.

FIG. 7 illustrates a formulation chamber 65, in opened view, comprising agent 66 in particle form, a release rate controlling polymer film 67 such as cellulose acetate or the like, and a filter 68. Filter 68 is a conventional filter with a pore size of 0.1 micron to 5 micron, and more preferably 0.22 micron or 0.45 micron, for removing bacteria and unwanted matter from the flowing solution thereby, aiding in maintaining a sterile solution. FIG. 8 illustrates formulation chamber 69 made with an internal pocket 70 for containing agent 71, for example the drug ephedrine sulfate. Pocket 70 is formed of a wall 72 made of a material such as a diffusional, semipermeable, or a microporous polymer that permits the passage of medical fluid into pocket 70 and agent solution formed therein from pocket 70. In an embodiment, when wall 72 is a semipermeable polymer, it can be provided with a delivery orifice to dispense the agent solution into chamber 69. Wall 72 is joined by adhesive, heat sealing or the like to wall 73 of chamber 69. Wall 73 is made of a material substantially impermeable to the passage of agent, medical fluid and agent solution formed therein. In operation, fluid enters chamber 69 and then into pocket 70, wherein it forms a solution containing the agent that passes into chamber 69 and then is administered therefrom to a recipient. The system in FIG. 8 allows regulation of fluid flow independently from agent delivery. Delivery is governed by the mass transport characteristics of membrane 72, and fluid flow is governed by a resistance element, for example, a flow regulator, in the fluid path.

The intravenous systems comprising the formulation chamber can be used, in one embodiment in fluid replacement, such as administering plasma, saline, or the like, and simultaneously administering a therapeutically effective amount of drug, or prodrug, or the like therewith; in another embodiment as in a method of electrolyte-balance requirement, such as supplying sodium, potassium, chloride ions, or the like with a drug in an active form, in an inactive form that is converted in the animal to an active form, or in a form that is made active in the drug chamber and administered therewith to an animal, such as a human patient in need of electrolyte restoration and an intravenous drug; and in a method of intravenous nutrition, such as supplying dextrose, and concomitantly administering a drug to a warm-blooded animal such as a patient in need of such therapies. The intravenous therapy system also can be used in the practice of veterinary medicine.

The novel and useful intention provides an apparatus and a method for the obtainment of precise control of agent release into an intravenous delivery system and for administration to a warm-blooded animal. While there has been described and pointed out features of the invention as applied to presently preferred embodiments, those skilled in the art will appreciate that various modifications, changes, additions, and omissions in the invention illustrated and described can be made without departing from the spirit of the invention.

I claim:

1. A drug formulation chamber for use with an intravenous delivery system for administering a beneficial drug at a controlled rate for the care of a patient on intravenous therapy, which formulation chamber is moisture proof and comprises:
    (a) a wall that surrounds an internal lumen;
    (b) an inlet in the wall of the formulation chamber adapted and sized for placing the formulation chamber into an intravenous delivery system and for letting an intravenously administrable fluid enter the formulation chamber;
    (c) a beneficial intravenously administrable drug in a therapeutically effective amount up to 20 grams in the formulation chamber, said drug in a pharmaceutically acceptable solid dosage form selected from the group consisting of crystalline, microcrystalline, particle, pellet, granule, powder, dried, lyophilized, compressed forms and friable layers, and wherein when the formulation chamber is in operation the beneficial drug is added to fluid that enters the formulation chamber at a rate regulated by the fluid flow through the intravenous delivery system and by the rate of dissolution of the solid dosage form in the fluid that enters the formulation chamber to provide a fluid drug formulation acceptable for intravenous therapy; and,
    (d) an outlet in the wall of the formulation chamber adapted and sized for placing the formulation chamber in an intravenous delivery system for letting the fluid drug formulation leave the formulation chamber.

2. A lightweight disposable drug formulation chamber comprising glass or plastic for use with an intravenous delivery system, which formulation chamber is moisture proof and comprises:
    (a) a wall that surrounds an internal lumen;
    (b) an inlet in the wall of the formulation chamber for letting an intravenously administrable fluid from an intravenous delivery system enter the formulation chamber;
    (c) a beneficial drug in a pharmaceutically acceptable form consisting of solid, crystalline, microcrystalline, particle, pellet, granule, powder, spray-dried and lyophilized forms in a therapeutically effective amount up to 20 grams in the formulation chamber, which beneficial drug, when the formulation chamber is in operation, is formulated in the formulation chamber with fluid that enters the formulation chamber at a rate regulated by fluid flow in the intravenous system and at a rate governed by the rate of solubility of the drug in the fluid that enters the formulation chamber to provide a fluid drug formulation comprising the drug in a physical-chemical form acceptable for intravenous administration; and,
    (d) an outlet in the wall of the formulation chamber for letting fluid drug formulation leave the formulation chamber and enter the intravenous delivery system.

3. A formulation chamber for use with an intravenous administration system, which formulation chamber is moisture proof and consists essentially of:
    (a) a wall that surrounds an internal space, said wall comprising a lightweight, disposable composition;
    (b) an inlet in the wall adapted and sized for placing the formulation chamber in an intravenous system and for letting an intravenously administrable fluid into the formulation chamber;
    (c) an outlet in the wall adapted and sized for placing the formulation chamber in an intravenous system and for letting an intravenously administrable fluid into the formulation chamber;
    (d) a beneficial drug in a therapeutically effective amount of about 5 milligrams to 20 grams for executing a prescribed theapeutic program in the formulation chamber, said drug in a pharmaceutically acceptable solid form selected from the group consisting of crystalline, particle, granule, powdered, lyophilized, friable and compressed forms, which solid forms, when the formulation chamber is in operation, mix with fluid that enters the formulation chamber at a rate governed by the rate of fluid flow and the rate of mixing with the fluid to form an intravenously acceptable fluid formulation, and which beneficial drug is carried from the formulation chamber by the fluid to a recipient on intravenous administration.

4. A method for adding a beneficial intravenously administrable solid drug to an intravenously acceptable fluid in an intravenous delivery system, wherein the method comprises:
   (a) admitting the intravenously acceptable fluid into a moisture proof formulation chamber, which formulation chamber comprises:
      (1) a wall that surrounds an internal space, which wall comprises a lightweight disposable material;
      (2) a fluid inlet and outlet means in the wall adapted and sized for placing the formulation chamber in an intravenous delivery system and for communicating with the internal space;
      (3) a beneficial drug in the formulation chamber in a therapeutically effective amount to 20 grams, said drug in a pharmaceutically acceptable solid form selected from the group consisting of crystalline, particle, pellet, granule, powder, dried and lyophilized forms; and,
   (b) adding the solid drug to the intravenously acceptable fluid that enters the formulation chamber at a combined rate comprising a rate governed by the rate of fluid flow into the formulation chamber, and at a rate governed by the rate of adding the drug to the fluid to form an intravenously acceptable fluid drug formulation.

5. An intravenous delivery system for providing an intravenously administrable fluid drug formulation for administering it to a recipient, wherein the system comprises in combination:
   (a) a container of an intravenously administrable fluid;
   (b) a moisture proof formulation chamber in fluid communication with the container, said formulation chamber comprising:
      (1) a wall surrounding an internal space;
      (2) fluid inlet and outlet means in the wall adapted and sized for placing the formulation chamber in an intravenous delivery system and for communicating with the internal space;
      (3) a beneficial intravenously administrable drug in a therapeutically effective amount to 20 grams, said drug in a pharmaceutically acceptable solid form selected from the group consisting of crystalline, particle, pellet, granule, powdered, dried, lyophilized, friable and compressed forms, which solid drug forms, when the delivery system is in operation, formulated with fluid that enters the chamber at a rate governed by the rate of fluid flow from the container into the chamber and at a rate governed by the rate of adding the drug to the fluid, thereby providing the intravenously administrable fluid drug formulation.

6. A drug formulation chamber shaped and sized for use with an intravenous delivery system for intravenous therapy, said formulation chamber moisture proof, lightweight, and disposable, and made of glass or plastic and comprises:
   (a) a wall that surrounds an internal lumen;
   (b) means in the wall of the formulation chamber for letting an intravenously administrable fluid that is a pharmaceutically acceptable carrier for a drug enter and leave the formulation chamber; and,
   (c) a beneficial drug in a pharmaceutically acceptable form for intravenous administration present in a therapeutically effective amount to 20 grams in the formulation chamber and, wherein when the formulation chamber is in communication with an intravenous delivery system, the drug is added in a pharmaceutically acceptable solid form selected from the group consisting of crystalline, particle, pellet, granule, powdered, dry and lyophilized forms to fluid that enters through the means into the formulation chamber at a rate regulated by fluid flow and at a rate regulated by mixing of the drug with the fluid, thereby providing a fluid drug formulation acceptable for intravenous therapy that leaves the formulation chamber through the means.

* * * * *